US009421175B2

(12) United States Patent
Larsen (10) Patent No.: US 9,421,175 B2
(45) Date of Patent: Aug. 23, 2016

(54) PREVENTION OF RETINOPATHY BY INHIBITION OF THE VISUAL CYCLE

(76) Inventor: Lars Michael Larsen, Charlottenlund (DK)

( * ) Notice: Subject to any disclaimer, the term of this patent is extended or adjusted under 35 U.S.C. 154(b) by 1583 days.

(21) Appl. No.: 10/593,261

(22) PCT Filed: Mar. 16, 2005

(86) PCT No.: PCT/DK2005/000176
§ 371 (c)(1),
(2), (4) Date: Jul. 11, 2007

(87) PCT Pub. No.: WO2005/087210
PCT Pub. Date: Sep. 22, 2005

(65) Prior Publication Data
US 2007/0249713 A1 Oct. 25, 2007

(30) Foreign Application Priority Data
Mar. 17, 2004 (DK) .................. 2004 00431

(51) Int. Cl.
*A61K 31/20* (2006.01)
*A61K 31/07* (2006.01)
*A61K 31/05* (2006.01)
*A61K 31/203* (2006.01)

(52) U.S. Cl.
CPC ............... *A61K 31/07* (2013.01); *A61K 31/05* (2013.01); *A61K 31/203* (2013.01)

(58) Field of Classification Search
CPC ...... A61K 31/05; A61K 31/203; A61K 31/07
See application file for complete search history.

(56) References Cited

U.S. PATENT DOCUMENTS

| 5,094,783 | A | * | 3/1992 | Muccio et al. ......... | C07C 57/26 554/214 |
|---|---|---|---|---|---|
| 5,552,369 | A | | 9/1996 | Findeisen et al. | |
| 5,552,396 | A | | 9/1996 | Heath, Jr. et al. | |
| 5,624,949 | A | | 4/1997 | Heath, Jr. et al. | |
| 5,674,862 | A | | 10/1997 | Heath, Jr. et al. | |
| 5,698,578 | A | | 12/1997 | Heath, Jr. et al. | |
| 5,710,145 | A | | 1/1998 | Engel et al. | |
| 5,824,685 | A | | 10/1998 | Campochiaro et al. | |
| 6,015,807 | A | | 1/2000 | Engel et al. | |
| 6,114,320 | A | | 9/2000 | Aiello et al. | |
| 2003/0032078 | A1 | | 2/2003 | Travis | |
| 2004/0219187 | A1 | * | 11/2004 | Olejnik et al. ....... | A61K 9/0051 424/426 |

FOREIGN PATENT DOCUMENTS

| EP | 0522226 A1 | 1/1993 |
|---|---|---|
| WO | 9958126 A1 | 11/1999 |
| WO | 0198294 A2 | 12/2001 |
| WO | 02072003 A2 | 9/2002 |
| WO | 02080935 A1 | 10/2002 |
| WO | 02080936 A1 | 10/2002 |
| WO | 02085400 A1 | 10/2002 |
| WO | 03004058 A1 | 1/2003 |
| WO | 03082081 A2 | 10/2003 |
| WO | 03097052 A2 | 11/2003 |
| WO | 03104178 A1 | 12/2003 |
| WO | 2005011741 A2 | 2/2005 |
| WO | 2005056010 A1 | 6/2005 |
| WO | 2005058304 A1 | 6/2005 |
| WO | 2005107707 A1 | 11/2005 |

OTHER PUBLICATIONS

Paul A. Sieving et al. "Inhibition of the visual cycle in vivo by 13-cis retinoic acid protects from light damage and provides a mechanism for night blindness in isotretinoin therapy", Proc. Nat. Acad. Sci. (USA), Feb. 13, 2001, vol. 98, No. 4, pp. 1835-1840.
Roxana A. Radu et al., "Treatment with isotretinoin inhibits lipofuscin accumulation in a mouse model of recessive Stargardt's macular degeneration", Proc. Nat. Acad. Sci. (USA), Apr. 15, 2003, vol. 100, No. 8, pp. 4742-4747.
Janet R. Sparrow, "Therapy for macular degeneration: Insights from acne", PNAS, Apr. 15, 2003, vol. 100, No. 8, pp. 4353-4354.
G. B. Arden, "The absence of diabetic retinopathy in patients with retinitis pigmentosa: implications for pathophysiology and possible", Br F Ophthalmol, 2001, vol. 85, pp. 366-370.
Lerman, S., "Ocular side effects of accutane therapy", Lens and Eye Toxicity Research, 1992, vol. 9(3-4), pp. 429-438.
Deviprasad R. Gollapalli et al., "Specfic inactivation of isomerohydrolase activity by 11-cis-retinoids", Science Direct, Biochimica et Biophysica Acta 1651 (2003) pp. 93-101.
Deviprasad R. Gollapalli et al., "All-trans-retinyl Esters Are the Substrates for Isomerization in the Vertebrate Visual Cycle", Biochemistry, Apr. 25, 2003, vol. 42 pp. 5809-5818.
Deviprasad R. Gollapalli et al., "RPE65 Operates in the Vertebrate Visual Cycle by Stereospecifically Binding All-trans-Retinyl Esters", Biochemistry, Sep. 17, 2003, vol. 42, pp. 11824-11830.
Paul S. Bernstein et al., "Mechanism of Action of Aromatic Amines That Short-Circuit the Visual Cycle", Biochemistry, 1986, vol. 25, pp. 3370-3377.
N Drasdo et al., "Effect of darkness on inner retinal hypoxia in diabetes" The Lancet, vol. 359, Jun. 29, 2002, pp. 2251-2253.
Anette Winston et al.,"Regulation of Isomerohydrolase Activity in the Visual Cycle", Biochemistry, Feb. 3, 1998, vol. 37, pp. 2044-2050.

(Continued)

*Primary Examiner* — Zohreh Fay
(74) *Attorney, Agent, or Firm* — Browdy and Neimark, PLLC (57) ABSTRACT

The invention relates to compounds capable of inhibiting the visual cycle and/or dark adaptation and their use for treatment and prevention of non-degenerative retinal diseases with specific emphasis on the prevention and treatment of diabetic retinopathy, retinopathy of prematurity, branch retinal vein occlusion, central retinal vein occlusion, open-angle glaucoma, veovascular glaucoma, and other diseases of the retinal and/or optic nerve where an imbalance between metabolic demand and blood supply contribute to the development of tissue damage. The invention furthermore relates to pharmaceutical compositions comprising such compounds.

9 Claims, 3 Drawing Sheets

(56) References Cited

OTHER PUBLICATIONS

G.B. Arden et al., "Does dark adaptation exacerbate diabetic retinopathy? Evidence and a linking hypothesis", Vision Research, vol. 38, 1998, pp. 1723-1729.
Anna Wrobel et al., "Antiangiogenic activity of agonist and antagonists of retinoid nuclear receptors", Przeglad Dermatologiczny, 1999, vol. 86, No. 4, pp. 339-346 (in Polish).
Michael F. Marmor, et al., "Albipunctate Retinopathy with cone Dysfunction and no Abnormality in the RDH5 or RLBPI Genes", Retina 2003 United States, vol. 23, vol. 4, pp. 543-546.
B. M. Calissendorff, "Retinal changes degeneration or side effects caused by etretinate therapy Tigason" Klin. Mbl. Augenheilk, vol. 194, 1989, pp. 187-189 (in German).
Tsutomu Oikawa et al., "Three novel synthetic retinoids, Re 80, Am 580 and Am 80, all exhibit anti-angiogenic activity in vivo", Europ J. of Pharmac., vol. 249, 1993, pp. 113-116.
Selig Hecht et al., "Rod-Cone Dark Adaptation and Vitamin A", Science, New Series, vol. 88, No. 2279, Sep. 2, 1938, pp. 219-221.
John E. Dowling et al., "Vitamin a Deficiency and Night Blindness", Proc. Natl. Acad. Sci. USA vol. 44, (1958) pp. 648-661.
Richard G. Weleber et al., "Abnormal Retinal Function Associated with Isotretinoin Therapy for Acne", Arch Opthalmol, vol. 104, Jun. 1986, pp. 831-837.
H. MacLean et al., "Abnormal night vision with isotretinoin therapy for acne", Clinical and Experimental Dermatol, vol. 20, p. 86, Jan. 1995.
Rosalie K. Crouch et al., "Retinoids and the Visual Process", Photochem. Photobiol., vol. 64, pp. 613-621.
F. T. Fraunfelder, et al., "Ocular Side Effects Possibly Associated with Isotretinoin Usage", Am. J. Opthalmol, vol. 132, 2001, pp. 299-305.
Wing C. Law et al., "The Molecular Basis of Retinoic Acid Induced Night Blindness" Biochem. Biophy. Res. Comm., vol. 161, No. 2, pp. 825-829.
Belinda M. Welsh et al., "Night blindness precipitated by isotretinoin in the setting of hypovitaminosis A", Australas J Dermatol, vol. 40, 1999, pp. 208-210.
G. P. Moss et al., "Nomenclature of Retinoids", Arch. Biochem., Biophys. vol. 224, No. 2, Jul. 15, 1983, pp. 728-731.
Brahma P. Sani et al., "Structural Characteristics of Synthetic Retinoids", Meth. in Enzymology, vol. 189, 1990, pp. 43-59.
Michael Klaus, "Structure Characteristics of Natural and Synthetic Retinoids" Meth. in Enzymology, vol. 189, (1990) pp. 3-14.
M. I. Dawson et al., "Synthetic Retinoic Acid Analogs: Handling and Characterization", Meth. in Enzymology, vol. 189, , 1990, pp. 15-43.
Gregory M. Acland et al., "Gene therapy restores vision in a canine model of childhood blindness", Nature genetics, vol. 28, May 2001, pp. 92-95.
T. Michael Redmond et al., "Rpe65 is necessary for production of 11-cis-vitamin A in the retinal visual cycle", Nature Genetics, vol. 20, Dec. 1998, pp. 344-351.
Paul S. Bernstein et al., "The Specific Inhibition of 11-cis-Retinyl Palmitate Formation in the Frog Eye by Diaminophenoxypentane, an inhibitor of Rhodopsin Regeneration", Vision Res., vol. 25, No. 6, 1985, pp. 741-748.
Brown, et al., "Visual toxicity of synthetic retinoids", British Journal of Ophthalmology, vol. 73, pp. 286-288, 1989.
Caffery, et al., "Ocular side effects of isotretinoin therapy", Journal of the American Optometric Association, vol. 59, No. 3, pp. 221-224, Mar. 1988.
Denman, et al., Abnormal night vision and altered dark adaptometry in patients treated with isotretinoin for acne, Journal of the American Academy of Dermatology, vol. 14, No. 4, pp. 692-693, Apr. 1986.
Feist, et al., "Visual Side Effects of Isotretinoin Therapy", Southern Medical Journal, vol. 80, No. 10, p. 1332, Oct. 1987.
Fraunfelder, et al., "Adverse Ocular Reactions Possibly Associated with Isotretinoin", American Journal of Ophthalmology, vol. 100, pp. 534-537, Oct. 1985.
Gross, et al., "Retinoids and the Eye", Dermatologic Clinics, vol. 10, No. 3, pp. 521-531, Jul. 1992.
Larsen "Statement of Proposed Amendments," filed on Aug. 18, 2010, Australian Patent Office, Australian Patent Application No. 2005221283.
Larsen "Statement of Proposed Amendments," filed on Jul. 12, 2010, Intellectual Property Office of New Zealand, New Zealand Patent Application No. 550340.
Larsen "Amendment After Acceptance," filed on Aug. 11, 2010, Intellectual Property Office of New Zealand, New Zealand Patent Application No. 550340.
Larsen "Amended Claims filed in response to Final Rejection", 2010, Chinese Patent and Trademark Office, Chinese Patent Application No. 200580015840.4.
Larsen "Response to Communication Under Article 96(2) EPC," filed on Aug. 8, 2007, European Patent Office, European Application No. 05715097.1-1216.
Arden. The absence of diabetic retinopathy in patients with retinitis pigmentosa: implications for pathophysiology and possible treatment. Br J Opthtalmol 85, 366-370 (2001).
Bernstein et al. Mechanism of action of aromatic amines that short-circuit the visual cycle. Biochemistry 25, 3370-3377 (1986).
Bershad. Developments in topical retinoid therapy for acne. Seminars in Cutaneous Medicine and Surgery, vol. 20, No. 3, 154-161 (2001).
Drasdo et al. Effect of drakness on inner retinal hypoxia in diabetes. The Lancet, 359, 2251-2253 (2002).
Kondo. Night blindness caused by 13-cis retinoic acid (Accutane). Journal of the Eye, 19(11), 1459-1460 (2002).
Zouboulis. Retinoids—which dermatological indications will benefit in the near future? Skin Pharmacol Appl Skin Physiol 14, 303-315 (2001).

* cited by examiner

PREVENTION OF RETINOPATHY BY INHIBITION OF THE VISUAL CYCLE

All patent and non-patent references cited in the application are hereby incorporated by reference in their entirety.

FIELD OF INVENTION

The present invention relates to compounds capable of inhibiting the visual cycle and/or dark adaptation and their use for treatment and prevention of non-degenerative retinal diseases with specific emphasis on the prevention and treatment of diabetic retinopathy, retinopathy of prematurity, branch retinal vein occlusion, central retinal vein occlusion, open-angle glaucoma, neovascular glaucoma, and other diseases of the retinal and/or optic nerve where an imbalance between metabolic demand and blood supply contribute to the development of tissue damage.

BACKGROUND OF INVENTION

Patients suffering from diabetes occasionally develop diabetic retinopathy, the leading cause of blindness of people aged 20-60.

Diabetic retinopathy is a non-degenerative disease of the small blood vessels of the retina, which is the light-sensitive tissue in the back of the eye. Diabetic retinopathy is related to the abnormally elevated levels of blood sugar in diabetes, and the retinal changes include impaired vascular function, vascular leakage, vascular congestion, vascular occlusion, tissue swelling (edema) and tissue ischemia. Metabolic hyperactivity and hyperfusion are also implicated in the development of diabetic retinopathy.

The lower grades of diabetic retinopathy are collectively called diabetic background retinopathy or nonproliferative diabetic retinopathy. Leakage of fluid from diseased retinal vessels may cause swelling of the center of the retina (the foeva, which is in the center of the macula) and hence cause blurred vision and severe visual loss secondary to diabetic macular edema. Reduced retinal perfusion secondary to microvascular occlusion may cause the growth of new vessels from intact vessel. Such neovascularizations (proliferative diabetic retinopathy) may cause preretinal hemorrhage, traction detachment of the retina, and severe visual loss. About half of the people with proliferative retinopathy also experience macular edema, which can occur at any stage of diabetic retinopathy.

The conventional primary means of treating diabetic retinopathy target its macular edema and proliferative retinopathy stages. The treatment consists of producing multiple circumscribed photocoagulation lesions of the outer layers of the retina, using, for instance, blue-green 514.5 nm light from an argon ion laser. Such lesions induce focal necrosis and permanent functional loss, but if applied properly, the treatment may result in improved preservation of some visual function rather than complete or incapacitating visual loss. The function of the center of the visual field is given special priority. The mechanism of action of photocoagulation treatment involves reduction of oxygen demand by removal of a large proportion of the retinal photoreceptors and enhanced drainage of fluid from the retina to the choroid, and probably also perfusion reduction.

If severe preretinal bleeding or traction from fibrotic proliferations occur, surgical removal of blood, fibrous tissue, and vitreous gel can be performed. Vitrectomy is usually accompanied by retinal photocoagulation treatment if this has not been completed on beforehand. Overall, photocoagulation and vitrectomy are successful only in reducing the rate of visual loss in patients with diabetic retinopathy to about half of the spontaneous rate. Photocoagulation has considerable drawbacks, because it is only moderately effective and because it invariably induces loss of vision corresponding to the location of the coagulation injury.

Once a patient has been diagnosed with diabetic retinopathy the risk of bleeding will always be present and repeated treatment may be needed. Diabetic retinopathy has no early warning signs and macular edema and proliferative diabetic retinopathy can develop without any premonitory symptoms, therefore diabetic retinopathy may develop undetected to the severe stages of the disease.

Currently, besides attempting to control levels of blood sugar, blood pressure and blood cholesterol, no method for prevention of diabetic retinopathy is known. A preventive mode of treatment would substantially reduce occurrence of eyesight loss in diabetic patients and ease the course of the disease. Furthermore, a modality of treatment that is better than conventional treatment or an effective adjunct to conventional treatment will be of considerable benefit to patients with diabetes.

Retinoids are a class of compounds with several functional activities consisting of four isoprenoid units joined in a head-to-tail manner (9). Several such compounds are vitamins or provitamins because they possess the biological activity of vitamin A, which is not synthesized in the body and must be derived from the diet. Retinoids are also hormones with intracrine activity and capable of binding to nuclear receptors resulting in the alteration of cell division and immune function.

Figure 1:
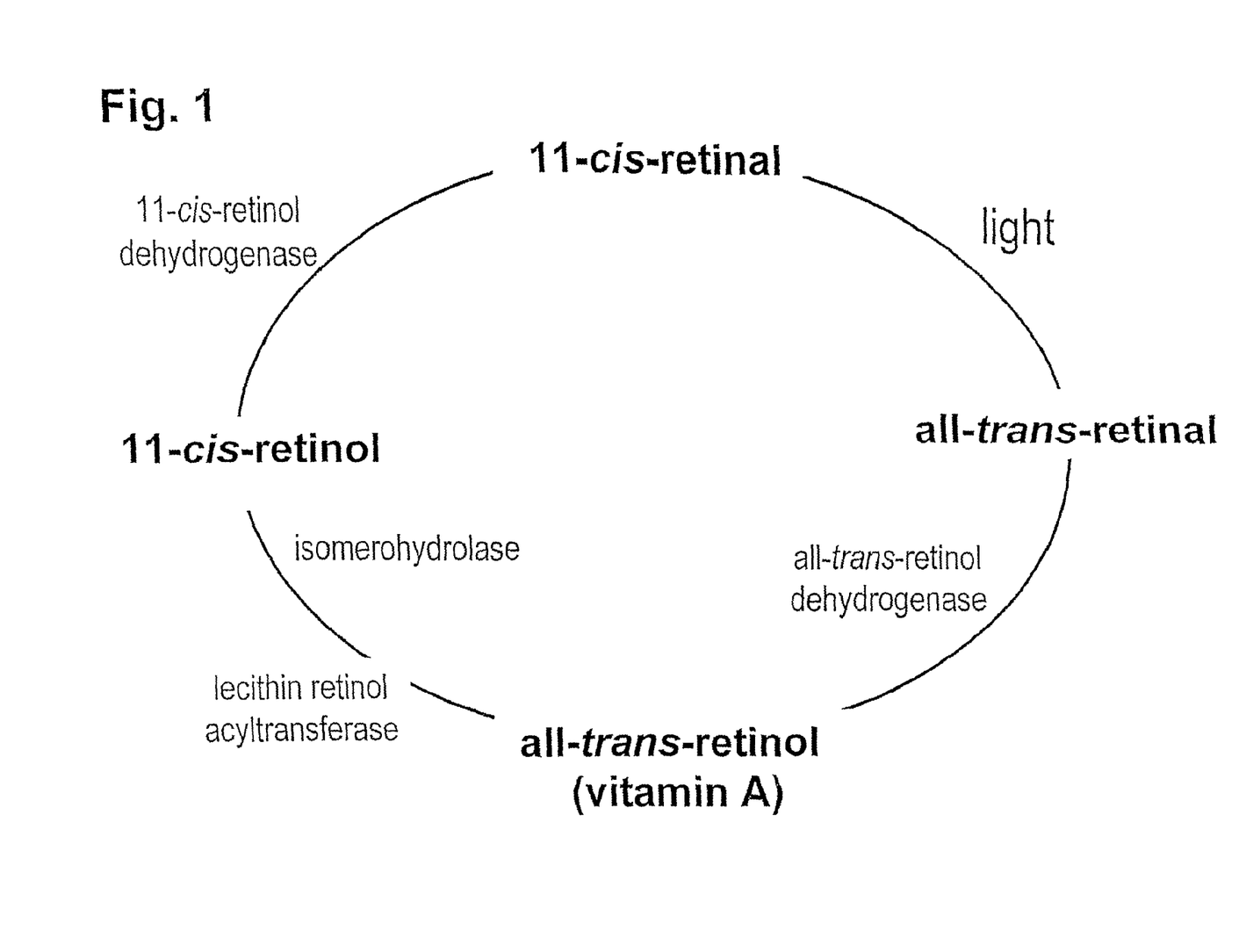
FIG. 1. Schematic representation of the visual cycle.
Figure 2:
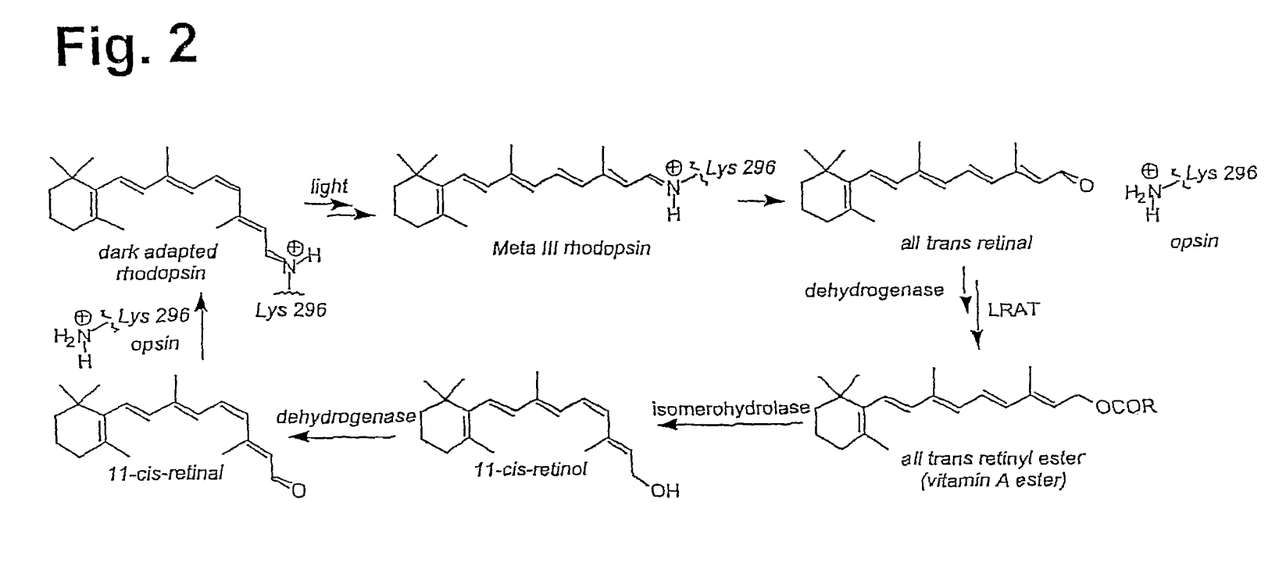
FIG. 2. Chemical structures of compounds of the visual cycle.
Figure 3:
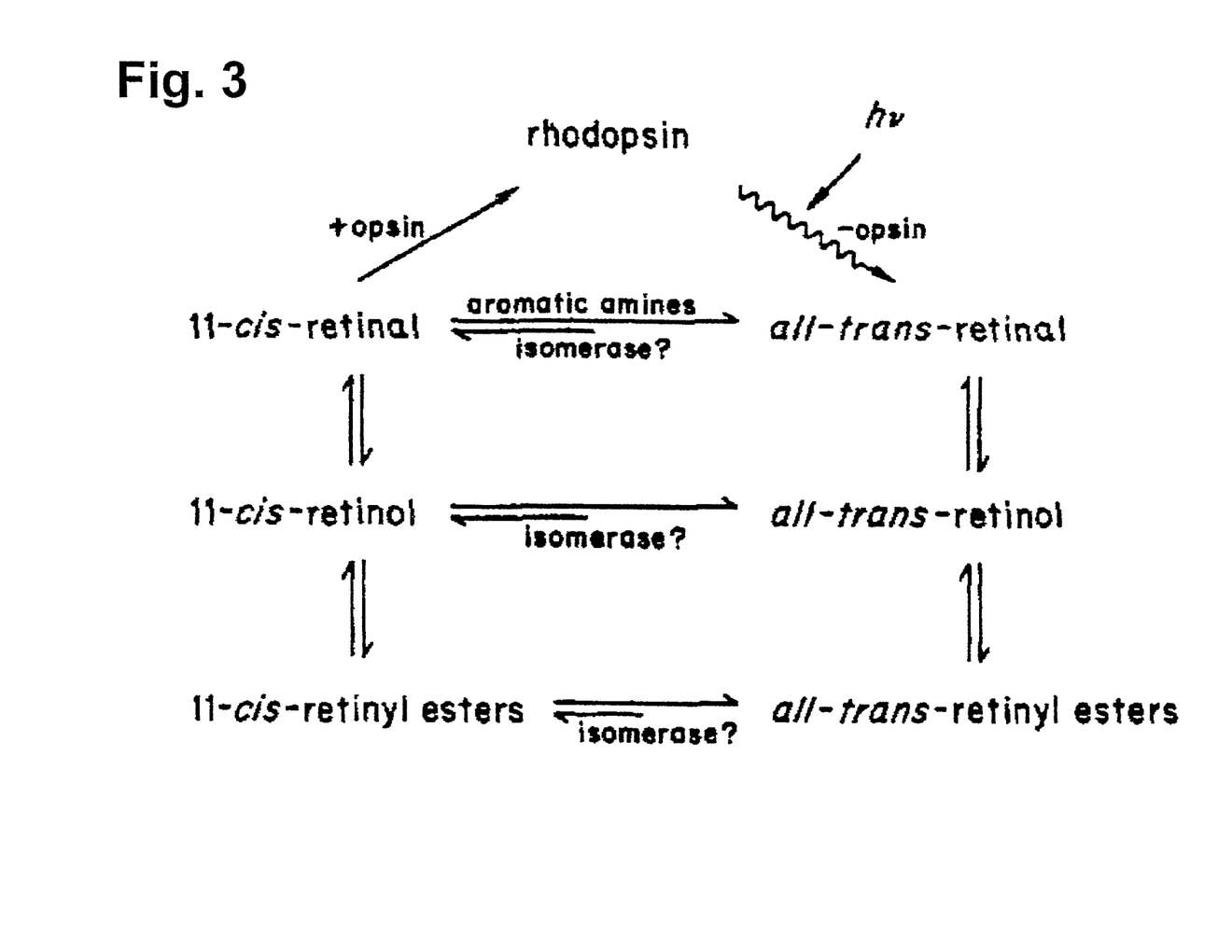
FIG. 3. Schematic representation of the proposed activity of aromatic amines in the visual cycle.

The visual response in vertebrates begins by a light-induced isomerisation of the rhodopsin chromophore, 11-cis-retinal, in the photoreceptor cells of the retina. Light bleaches 11-cis-retinal to all-trans-retinol (vitamin A), which cannot be synthesized de novo by mammals. The bleaching of the purple-red rhodopsin to visual yellow initiates retinal visual signalling. The recovery mechanism from bleach requires reconversion of the chromophore to 11-cis-retinal by a multiple of enzymatic reactions called the visual cycle (FIGS. 1, 2 and 3). This process takes place in the retinal pigment epithelium (RPE), a cell layer lying adjacent to the photoreceptor cells (1).

The colour and sensitivity to light of the rhodopsin protein in the photoreceptors depend upon the presence of 11-cis-retinal. Disruption of the visual cycle retards restoration of the visual function after exposure to bright light. Notably dark adaptation and night vision are deficient in subjects with deficient uptake of vitamin A (2). Night blindness can also be induced by dietary substitution of vitamin A with retinoic acid in rats (3).

The retinoids comprise a group of natural and synthetic compounds with structural similarities and affinity for biological receptors for vitamin A (retinol). Retinoids possess dual functional activities as hormones and vitamins, respectively. They stimulate nuclear retinoid receptors controlling cell division and immune function, and they absorb photons in the retina and then initiate the visual (vitamin A) cycle.

A synthetic analogue of vitamin A, the retinoid isotretinoin (13-cis-retinoic acid), is commonly used for treatment of severe nodular acne and various other skin disorders for almost two decades. Known side-effects of isotretinoin treatment are night blindness and excessive glare sensitivity (4-6) and experiments have shown that isotretinoin exerts its effect by inhibiting the processing of vitamin A in the retina and the RPE (7-8). Other retinoids, such as the 11-cis-retinoids have been shown to inhibit enzymes involved in catalyzing processes of the visual cycle and thereby slow dark adaptation in treated subjects (13).

During dark adaptation, the photoreceptor layer removes considerable amounts of oxygen from the inner retina leading to an unusually low oxygen tension. Retinal hypoxia has been shown to play a major role in the development of diabetic retinopathy and elimination of periods with full dark adaptation by low levels of background light at night has been suggested as a therapeutic against diabetic retinopathy (14).

SUMMARY OF INVENTION

It has now surprisingly been found that compounds capable of inhibiting the visual cycle and/or dark adaptation can be used for the prevention and/or treatment of diabetic retinopathy. This principle also applies to other ischemic and/or hypoxic diseases of the retina and the optic nerve, the latter consisting of nerve cell axons that are extensions from the ganglion cell bodies of the retina. Such conditions include retinopathy of prematurity, branch retinal vein occlusion, central retinal vein occlusion, open-angle glaucoma, and neovascular glaucoma.

Accordingly, in a first main aspect, the invention relates to the use of at least one compound capable of inhibiting the visual cycle and/or dark adaptation in an individual in the manufacture of a medicament for prevention or treatment of a non-degenerative retinal disorder, or associated symptoms and complications thereof, in a mammal, in particular a human being Similarly, the invention relates, in a main aspect, to a method for prevention and/or treatment of a non-degenerative retinal disorder, or associated symptoms and complications thereof, in a mammal, comprising administering to said mammal a pharmaceutically efficient amount of at least one compound capable of inhibiting the visual cycle and/or dark adaptation in an individual.

Thus, the present invention has the potential to eradicate the most predominant causes of blindness of people of the working ages in industrialized countries and substantially reduce the sufferings of patients with diabetes.

In a further aspect the present invention is directed to a medicament for prevention or treatment of a non-degenerative retinal disorder comprising at least one compound capable of inhibiting the visual cycle and/or dark adaptation in an individual, as an active ingredient.

Thus, there is also provided a pharmaceutical composition suitable for intravitreal implantation comprising a pharmaceutically effective amount of at least one compound capable of inhibiting the visual cycle and/or dark adaptation.

DEFINITIONS

The terms "treatment" and "treating" as used herein refer to any treatment of a disease in a mammal, particularly a human being, and generally include inhibiting the disease, i.e. arresting its development, or relieving the disease, i.e. causing regression of the disease. Treating also refers to providing a beneficial alteration in one or more of the symptoms of a disease state or reducing or eliminating the disease state itself. It will be appreciated that a beneficial alteration can include transitory or permanent reduction or elimination of the symptom.

The terms "prevention" and "preventing" as used herein refer to prevention of the occurrence of a disease in a subject that may be predisposed to a disease but has not yet been diagnosed as having it. It will also be appreciated that "prevention" and "preventing" can also involve a reduction in the likelihood of adverse consequences of a pathological state. Thus, "prevention" and "preventing" as used herein can also refer to prophylaxis.

For therapeutic purposes the term "a pharmaceutically efficient amount" means the amount of a pharmaceutical agent or multidrug therapeutic which elicits a positive response on at least one symptom of a disease state, or which acts prophylactically to reduce the likelihood of at least one pathological symptoms or consequences of a disease state, i.e. to inhibit the onset or progression of the disease.

The term "administering" in the context of "administering to a mammal" refers to delivering the therapeutic agents in question to an organism. Administration can be systemic, topical, or local administration as described herein, or the implantation of a slow-release device to the subject.

As used herein, "therapeutic agent" means any agent useful for therapy.

"Inhibition of the visual cycle" or "inhibiting the visual cycle" as used herein means stopping, eliminating, or slowing down any or more processes of the visual cycle, for example inhibition of the formation of 11-cis-retinoids, such as 11-cis-retinal, as measured invasively or in organ culture by spectrophobic assays, such as inhibition of the conversion of 11-cis-retinal into dark adapted rhodopsin as measured invasively or in organ culture by spectrographic assays, for example inhibition of one or more enzymes in the visual cycle leading to decrease of dark adapted rhodopsin, such as eliminating the photoisomerization step of the cycle by catalyzing the isomerization of 11-cis-retinal to all-trans-retinal, or for example by depletion of stores of 11-cis-retinoids. In vivo monitoring of such effects can be made using flicker photometric determination of the spectral absorption of the fundus of the eye or dark adaptometry using the method of Goldmann-Weeker or electroretinographic assessment of scotopic and photopic retinal function.

The term "lower" when used herein in connection with a chemical group means having 1 to 6 carbon atoms, preferably 1 to 4 carbon atoms, most preferably 1 or 2 carbon atoms. According, a "lower alkyl" when used herein means an alkyl group having 1 or 6 carbon atoms, preferably 1 to 4 carbon atoms, most preferably 1 or 2 carbon atoms, i.e. a methyl or ethyl group.

DETAILED DESCRIPTION OF THE INVENTION

The invention relates to the use of compounds capable of inhibiting the visual cycle and thereby slowing down the regeneration of the photopigment of the retina for prevention and/or treatment of diabetic retinopathy, of retinopathy of prematurity, and of other non-degenerative disorders of the eye.

The visual pigment rhodopsin in vertebrates contains an 11-cis-retinal protonated Schiff base and during visual response a photon absorbed by a rhodopsin molecule causes a cis to trans photoisomerization of the rhodopsin chromophore 11-cis-retinal to all-trans-retinal in the outer segment discs of rod photoreceptors (FIG. 2). The bleached photopigment activates the signal transduction cascade leading to membrane hyperpolarization and retinal visual signalling.

Recovery from bleach and dark adaptation involves rhodopsin regeneration by the reconversion of the all-trans-retinol into 11-cis-retinal by enzymatic reactions in completion of the visual cycle, also called the vitamin A cycle (FIG. 1). During the visual cycle all-trans-retinal is reduced to all-trans-retinol (vitamin A) by all-trans-retinol dehydrogenase. The all-trans-retinol is released from the outer segment disc and taken up by an underlying RPE cell. Lecithin retinol acyltransferase (LRAT) catalyzes the generation of all-trans-retinyl esters from vitamin A and isomero-hydrolase processes the esters into 11-cis-retinol, which is oxidized by 11-cis-retinol dehydrogenase to form 11-cis-retinal chromophore.

In several animal models suffering from retinal disorders light accelerates retinal degeneration and dark rearing has been shown to prolong rod cell survival. Furthermore, slowing of rhodopsin regeneration or the absence of rhodopsin in knockout mice confer protection from light damage. The slowing of rhodopsin regeneration by inhibition of the formation of 11-cis-retinal provides a therapeutic strategy for non-degenerative retinal disorders by reducing the number of photo-isomerization events.

The protein RPE65 plays an important role in visual cycle function. RPE65 knockout mice are unable to produce substantial levels of 11-cis-retinoids and all-trans-retinyl esters where found to accumulate in RPE cells of these mice (16). Recovery of visual function after transgenic correction of this defect has demonstrated that chronic inhibition of the visual cycle is possible without conferring irreparable damage to the retina (15).

Compounds Capable of Inhibiting the Visual Cycle and/or Dark Adaptation

Examples of compounds capable of slowing the visual cycle and/or dark adaptation include, but are not limited, to the following compounds.

In a first main embodiment, the invention relates to the use described herein of a compound of the formula I:

(formula I)

wherein R1 is:
a lower alkyl, preferably CH2CH3 or CH3, having a single bond to the carbon at position 9 (C9), wherein the bond between C9 and R2 preferably is a double bond or CH2OH or CHO or CF3 or CH2 with a double bond to C9, there being a single bond between C9 and R2, or a bond from C9 to R2 (resulting in a triple bond between C9 and R2) or OH (single bond to C9)

and wherein R2 is:

(formula II)

wherein R11 is selected from the group consisting of:
an alcohol, such as —CH2OH, an aldehyde, such as —CHO, a carboxy group (—COOH), a lower alkyl, such as —CH3, an ether, such as —CH2OCH3, —CH2OC4H9, —CH2OC6H5 or —CH2OC8H17, an ester, such as —CH2OCOCH3, a amine derivative, such as —CH2NHCOCH3, —CH2NHCOC6H5, or —CH2NCH3COCH3, —CH3COC6H5, CH=NOH, CH=NNHCOCH3, CH=C(COCH2CH2CH3)2, —CH=C(COCH2)2, CH=C(COCH2)2CH2CH=C(COCH2CH2)2CH2, —COOCH3, —COOCH2H5, COZ where Z is an amino acid such as glycine, leucine, phenylalanine, or tyrosine, —CONHC2H5, —CONHC3H7, —CONH2-C2H4OH, —CONH2-C3H6OH, —CONH3-C3H6OH, —CONHC6H5, —CONH2-C6H4OH, —CONH4-C6H4OH, CONH2-C6H4COOH, CONH4-C6H4-COOH, a bromoacetate, such as —CH2OCOCH2Br, a chloroacetate, such as —CH2OCOCH2Cl, a ethoxycarbonyl, such as —COOCH2CH3, an N-alkylamide, such as —CONHR, wherein R is an alkyl, preferably 4-hydroxy-phenyl or ethyl, a COOR group wherein R is beta-D-glucuronide; an ethyl sulfone group; an ethyl ester group; and an alkoxycarbonyl group, such as ethoxycarbonyl;

and wherein R12 is:
a lower alkyl, preferably CH3 or CH2CH3, or CH2OH or CHO or CF3,
or R2 is a substituted aryl or heteroaryl, such as:

(formula III)

(formula IV)

wherein R13 is:
a carboxy (—COOH) group or
an alcohol (e.g. —CH2OH) group or
an aldehyde (e.g. —CHO) group or
a bromoacetate (—CH2OCOCH2Br) group or
a chloroacetate (—CH2OCOCH2Cl) group or
a ethoxycarbonyl (—COOCH2CH3) group or
an N-alkylamide (—CONHR) group (wherein R is an alkyl, preferably 4-hydroxy-phenyl or ethyl) or
a COOR group wherein R is beta-D-glucuronide or
an ethyl sulfone group or
an ethyl ester group or
an alkoxycarbonyl group, such as ethoxycarbonyl;
and wherein Y is C or N or S or O or R2 is
O (having a double bond to C9)
and wherein R3 is OH or a lower alkyl or H or CH or CHRCH3 (wherein R is a double bond to R4),
and wherein R4 is H or CH or OH or a lower alkyl, such as CH3, and wherein R5 is OH or a lower alkyl, such as CH3, or H or O (double bond to atom at position 3) or absent, and wherein R6 is OH or a lower alkyl, such as CH3, or H or absent or a bond to R5 (if R5 is O) or a bond to C4, and wherein R7 is alkoxy, such as methoxy, or OH or a lower alkyl, such as CH3, or H or 3-(1-adamantyl)-4-methoxyphenyl, and wherein R8 is OH or a lower alkyl, such as CH3, or H or a bond to C6, and wherein R9 is OH or a lower alkyl, such as CH3, or H, and wherein R10 is OH or a lower alkyl, such as CH3, or H or a bond to C5, and wherein X is C or N or S or O.

wherein each of R1, R3, R4, R5, R6, R7, R8, R9, R10, R11, R12 and R13, is optionally substituted one or more times with a lower alkyl group, such as a methyl group or an ethyl group, with the proviso that when R2 is formula II and R1, R4, R9 and R12 are all CH3, and R3, R5, R6, R7 and R8 are all H and R11 is a carboxy group, the configuration is not 9-cis (2E,4E,6Z,8E) or all-trans, and the proviso that when R2 is formula II and R1, R4, R9 and R12 are all CH3, and R3, R5, R6, R7 and R8 are all H and R11 is an alcohol group, the configuration is not all-trans.

"Conventional" Retinoids

In a first preferred embodiment, the invention relates to the use of a compound according to formula 1, wherein the compound is a conventional retinoid, i.e. a retinoid according to the definition of the IUPAC-IUB Joint Commission on Biochemical Nomenclature which states that "retinoids are a class of compounds consisting of four isoprenoid units joined in a head to tail manner. All retinoids may be formally derived from a monocyclic parent compound containing five carbon-carbon double bonds and a functional group at the terminus of the acyclic portion" (9). The basic retinoid structure is generally subdivided into three segments, namely the polar terminal end, the conjugated side chain, and the cyclohexenyl ring. The basic structures of the most common natural retinoids are called retinol, retinaldehyde, and retinoic acid. Preferred retinoids of this invention are retinoids capable of inhibiting the visual cycle.

In this preferred embodiment, X is C, R1 has a single bond to the carbon at position 9, there is a double bond between the carbon at position 9 and R2, and R2 is a group of formula II:

(formula II)

Thus, in this embodiment, said compound has the formula V:

(formula V)

wherein the configuration of the four isoprenoid units can be all trans (E) (as illustrated above), or one or more can be cis (Z), and wherein R1-R12 are as defined above.

In a preferred embodiment, the configurations around the carbon-carbon double bands are all-trans (2E,4E,6E,8E) or 9-cis (2E,4E,6Z,8E), or 11-cis (2E,4Z,6E,8E), or 13-cis (2Z,4E,6E,8E).

In a preferred embodiment of the compound of formula V, R3 is H.

In another preferred embodiment of the compound of formula V, R4 is CH3.

In a more preferred embodiment of the compound of formula V, R3 is H and R4 is CH3.

In another preferred embodiment of the compound of formula V, R5 is H.

In another preferred embodiment of the compound of formula V, R6 is H.

In another preferred embodiment of the compound of formula V, R7 is H.

In another preferred embodiment of the compound of formula V, R8 is H.

In another preferred embodiment of the compound of formula V, R9 is CH3.

In another preferred embodiment of the compound of formula V, R10 is CH3.

In a more preferred embodiment of the compound of formula V, R5 is H and R6 is H and R7 is H and R8 is H and R9 is CH3 and R10 is CH3.

In a highly preferred embodiment of the compound of formula V, R3 is H, and R4 is CH3, and R5 is H, and R6 is H, and R7 is H, and R8 is H, and R9 is CH3, and R10 is CH3.

In another preferred embodiment of the compound of formula V, R5 is O and R6 is a bond to R5. Thus, in this embodiment, the carbon atom at position 3 of the ring forms a double bond with an oxygen. A non-limiting, but preferred, example of such a compound is 4-oxo-isotretinoin.

In a more preferred embodiment of the compound of formula V, R3 is H and R4 is CH3, and R5 is O and R6 is a bond to R5, and R7 is H, and R8 is H, and R9 is CH3, and R10 is CH3.

In another preferred embodiment of the compound of formula V, R3 is H, and R4 is CH3, and R5 is H, and R6 is H, and R7 is methoxy, and R8 is CH3, and R9 is CH3, and R10 is H.

In a preferred embodiment, R11 in formula V is selected from the group consisting of:
a carboxy (—COOH) group,
an alcohol (e.g. —CH2OH) group,
an aldehyde (e.g. —CHO) group,
a bromoacetate (—CH2OCHCH2Br) group,
a chloroacetate (—CH2OCHCH2Cl) group,
a ethoxycarbonyl (—COOCH2CH3) group,
an N-alkylamide (—CONHR) group (wherein the alkyl (R) is preferably 4-hydroxy-phenyl or ethyl), and
a COOR group, wherein R is beta-D-glucuronide.

In a more preferred embodiment, R11 is selected from the group consisting of:
an alcohol (e.g. —CH2OH) group,
an aldehyde (e.g. —CHO) group,
a bromoacetate (—CH2OCHCH2Br) group,
a chloroacetate (—CH2OCHCH2Cl) group,
a ethoxycarbonyl (—COOCH2CH3) group,
an N-alkylamide (—CONHR) group (wherein the alkyl (R) is preferably 4-hydroxy-phenyl or ethyl), and
a COOR group wherein R is beta-D-glucuronide.

In another more preferred embodiment, R11 is selected from the group consisting of:
a carboxy (—COOH) group,
an aldehyde (e.g. —CHO) group,
a bromoacetate (—CH2OCHCH2Br) group,
a chloroacetate (—CH2OCHCH2Cl) group, a ethoxycarbonyl (—COOCH2CH3) group,
an N-alkylamide (—CONHR) group (wherein the alkyl (R) is preferably 4-hydroxy-phenyl or ethyl), and
a COOR group wherein R is beta-D-glucuronide.

In a further preferred embodiment of the compound of formula V, R1 is CH3.

In another preferred embodiment of the compound of formula V, R12 is CH3.

For the compound of formula V, it is preferred that if R1, R4, R9 and R12 are all CH3, and R3, R5, R6, R7 and R8 are all H, and R11 is a carboxy group, then the configuration is not 9-cis (2E,4E,6Z,8E) or all-trans.

It is furthermore preferred for the compound of formula V that if R1, R4, R9 and R12 are all CH3, and R3, R5, R6, R7 and R8 are all H, and R11 is an alcohol group, then the configuration is not all-trans.

In a highly preferred embodiment, the compound of formula V is selected from the group consisting of: isotretinoin (13-cis-retinoic acid), 11-cis-retinol, 11-cis-retinal, 11-cis-retinyl bromoacetate, acitretin, etretinate, fenretinide, 4-oxo-isotretinoin, motretinide, retinaldehyde, all-trans-retinyl bromoacetate, all-trans-retinyl chloroacetate, and retinoyl betaglucoronide.

Compounds for use according to the invention also include side-chain modified cis and multi-cis retinoids such as, but not limited to, 13-cis-retinoic acid derivatives such as 13-cis-retinoic acid, N-ethyl-13-cis-retinamide, N-(2-hydroxyethyl)-13-cis-retinamide, N-(4-hydroxyphenyl)-13-cis-retinamide, N-(13-cis-retinoyl) leucine, and N-(13-cis-retinoyl) phenylalanine, bifunctional retinoic acid analogues such as 14-carboxyretinoic acid, ethyl 14-(ethoxycarbonyl) retinoate, and 14-[(ethylamino) carbonyl]-13-cis-retinoic acid. The compounds also include aldehydes, alcohols, or esters of 11-cis-retinoid, such as, but not limited to, 11-cis-retinol, 11-cis-retinal, and 11-cis-retinyl bromoacetate. The compounds also include ring-modified analogues such as the ring-modified all-trans-retinoic acid analogues, including but not limited to α-retinoic acid, 4-hydroxyretinoic acid, phenyl analogue of retinoic acid, 4-methoxy-2,3,6-trimethylphenyl analogue of retinoic acid, 5,6-dihydroretinoic acid, 4-oxoretinoic acid, 3-pyridyl analogue of retinoic acid, dimethylacetylcyclopentenyl analogue of retinoic acid, 2-furyl analogue of retinoic acid, and the 3-thienyl analogue of retinoic acid. Ring-modified retinoids also include retinoid analogues in which the cyclohexenyl ring is replaced by related structures.

Retinoids for use in the invention also include side-chain modified all-trans-retinoic acid analogues such as a $C_{15}$ analogue of retinoic acid, a $C_{17}$ analogue of retinoic acid, a $C_{22}$ analogue of retinoic acid, an aryltriene analogue of retinoic acid, 7,8-dihydroreltinoic acid, 8,10-dihydroretinoic acid, 11,12-dihydroretinoic acid. Other side chain modified retinoids include retinol, retinoic acid, and other retinoids with a partially or completely hydrogenated side chain. Still other retinoids having modified side chain include, but are not limited to, retinol or retinoic acid derivatives in which selected double bonds of the side chain are replaced with amide, sulfonamide, or other groups such as, but not limited to, p-(5,6,7,8-tetrahydro-15 5,5,8,8-tetramethyl-2-haphtalene-carboxamido) benzoic acid. Other suitable compounds include both ring- and side-chain-modified analogues of all-trans-retinoic acid including, but not limited to (E)-4-[2-(5,6,7,8-tetrahydro-5,5,8,8-tetramethyl-2-naphthalenyl)-1-propenyl]benzoic acid, (E)-4-[2-(5,6,7,8-tetrahydro-8,8-dimethyl-2-naphthalenyl)-1-propenyl]benzoic acid, (E)-4-[2-(5,6,7,8-tetrahydro-5,5,8,8-tetramethyl-2-naphthalenyl) carbamolyl]benzoic acid, (E)-4-[2-(5,6,7,8-tetrahydro-5,5,8,8-tetramethyl-2-naphthalenyl) carboxamido]benzoic acid, (E)-4-[2-(2,3-dihydro-1,1,2,3,3-pentamethyl-1H-inden-5-yl)-1-propenyl] benzoic acid, 6-(5,6,7,8-tetrahydro-5,5,8,8-tetramethyl-2-naphthalenyl)-2-naphthalenecarboxylic acid, 6-(5,6,7,8-tetrahydro-5,5,8,8-tetramethyl-2-naphtalenyl)-5-methyl-2-naphthalenecarboxylic acid, 6-(5,6,7,8-tetrahydro-5,5,8,8-tetramethyl-2-naphtalenyl)-6-benzo[b]thiophen-ecarboxylic acid, 4-(5,6,7,8-tetrahydro-5,5,8,8-tetramethyl-2-anthracenyl)benzoic acid, and (E)-4-[3-(3,5-Di-tert-butylphenyl)-3-oxo-1-propenyl]benzoic acid. Detailed descriptions of these and other retinoids can be found (10-12). Other preferred retinoids include glucuronic acid, retinyl β-glucuronide, and retinoyl β-glucuronide.

Arotinoids

In another main embodiment, the invention relates to the use of a compound of formula I, wherein R1 has a single bond to the carbon at position 9, and wherein there is a double bond between the carbon at position 9 and R2, and wherein R2 is a substituted aryl or heteroaryl, such as

Thus, in this embodiment, said compound has the formula VI:

(formula VI)

In a preferred embodiment of the compound of formula VI, R3 and R4 are both CH and are connected by a double bond.

More preferably, R3 and R4 are both CH and are connected by a double bond, and R5 is CH3 and R6 is CH3 and R7 is H and R8 is H and R9 is CH3 and R10 is CH3 and X is C and Y is C, thus giving the formula VII:

(formula VII)

In a preferred embodiment of the compound of formula VII, R13 is selected from the group consisting of: a carboxy (COOH) group, an ethyl sulfone group, and an ethyl ester group.

In another preferred embodiment of the compound of formula VII, R1 is CH3.

In a highly preferred embodiment, the compound of formula VII is selected from the group consisting of: arotinoid ethyl ester, arotinoid-free carboxylic acid and arotinoid ethyl sulfone.

Bexarotene-Like Compounds

In a further embodiment, the invention relates to the use of a compound of formula I, wherein X is C, and R1 is CH2, and R1 has a double bond to C9, i.e. there being a single bond between C9 and R2, and wherein R2 is a substituted aryl or heteroaryl, such as:

Thus, in this embodiment, said compound has the formula VIII:

(formula VIII)

In a preferred embodiment of the compound of formula VIII, R3 and R4 are both CH and are connected by a double bond.

In another preferred embodiment of the compound of formula VIII, R4 is CH and R3 is CHRCH3, wherein R is a double bond to R4.

In a further preferred embodiment of the compound of formula VIII, one or more, preferably all, of: R5, R6, R9 and R10 are CH3.

In a further preferred embodiment of the compound of formula VIII, R7 and R8 are both H.

In a further preferred embodiment of the compound of formula VIII, Y is C.

In a further preferred embodiment of the compound of formula VIII, R13 is a carboxy group.

In a highly preferred embodiment, the compound of formula VIII is bexarotene.

Tazarotene-Like Compounds

In a further embodiment, the invention relates to the use of a compound of formula I, wherein R1 is a bond from the carbon at position 9 to R2, resulting in a triple bond between C9 and R2, and wherein R2 is a substituted aryl or heteroaryl, such as:

Thus, in this embodiment, said compound has the formula IX:

(formula IX)

In a preferred embodiment of the compound of formula IX, R3 and R4 are both CH and form a double bond.

In another preferred embodiment of the compound of formula IX, R4 is CH and R3 is CHRCH3 (wherein R is a double bond to R4).

In a further preferred embodiment of the compound of formula IX, R9 and R10 are both CH3.

In a further preferred embodiment of the compound of formula IX, R7 and R8 are both H.

In a further preferred embodiment of the compound of formula IX, X is S and R5 and R6 are absent.

In a further preferred embodiment of the compound of formula IX, Y is N.

In a further preferred embodiment of the compound of formula IX, R13 is a alkoxycarbonyl group, most preferably an ethoxycarbonyl group.

In a highly preferred embodiment, the compound of formula IX is tazarotene.

Adapatene-Like Compounds

In a further embodiment, the invention relates to the use of a compound of formula I, wherein X is C, and R1 is OH (single bond to C9) and R2 is O (double bond to C9), and wherein R3 and R4 are both CH and are connected by a double bond, and wherein R6 is a bond to the carbon atom at position 4, and wherein R8 and R10 are a bond between C5 and C6.

Thus, in this embodiment, said compound has the formula X:

(formula X)

In a preferred embodiment of the compound of formula X, R5 is H and R9 is H.

In another preferred embodiment of the compound of formula X, R7 is 3-(1-adamantyl)-4-methoxyphenyl.

In a highly preferred embodiment, the compound of formula X is adapalene.

DAPP

DAPP [1,5-bis(p-aminophenoxy)pentane] is an example of a well-characterized non-retinoid inhibitor of dark adaptation. DAPP and monofunctional analogues of DAPP, such as p-phenitidine, act by impairing formation and storage of all 11-cis-retinoids in the vertebrate eye (17). The major requirements for a group of inhibitors of the visual cycle and/or dark adaptation of the phenitidine-type are suggested to consist of an aromatic amino group that can form a Schiff base with retinal and a moderately hydrophobic tail in para or meta position (18). These diverse compounds have a common ability to catalyze the energetically favoured isomerization of 11-cis-retinal to all-trans-retinal and are proposed to cause a chemical short-circuit of the visual cycle (FIG. 3).

A large number of retinoids and other compounds to be used according to the invention are commercially available (e.g. from Sigma-Aldrich Co., St. Louis, Mo., USA or from F. Hoffmann-La Roche Ltd., Basel, Switzerland, etc.).

In an important embodiment of the present invention, it should be appreciated that retinoids capable of inhibiting the visual cycle do not include all-trans-retinol (vitamin A), a substrate for LRAT in the visual cycle.

Compounds of the present invention include all known compounds, including retinoids, effective of inhibiting the visual cycle and/or dark adaptation in a subject. In one preferred embodiment of the present invention the at least one compound is effective of specifically inhibiting at least one enzyme of the visual (vitamin A) cycle and thereby slowing down the formation of 11-cis-retinal. In more preferred embodiments of the present invention the at least one compound is capable of inhibiting isomerohydrolase, all-trans-retinol dehydrogenase and/or lecithin retinol acyltransferase (LRAT).

In preferred embodiments of the present invention, the at least one compound is effective of inhibiting the visual cycle in a subject resulting in an inhibition of dark adaptation in said subject as determined by conventional methods as described herein.

In preferred embodiments of the present invention, the at least one compound is selected from a group consisting of isotretinoin (13-cis-retinoic acid), 11-cis-retinol, 11-cis-retinal, 11-cis-retinyl bromoacetate, acitretin, adapalene, bexarotene, etretinate, fenretinide, 4-oxo-isotretinoin, tazarotene, motretinid, arotinoid ethyl ester (Ro 13-6298), arotinoid-free carboxylic acid, arotinoid ethyl sulfone (etaro-tene, Ro 15-1570), retinaldehyde, all-trans-retinyl bromoacetate, all-trans-retinyl chloroacetate, and retinoyl beta-glucoronide.

In a preferred embodiment of the present invention the at least one compound comprises at least one 11-cis-retinoid, such as 11-cis-retinol, 11-cis-retinal, and 11-cis-retinyl bromoacetate, and/or at least one 13-cis-retinoid, such as 13-cis-retinoic acid. In another preferred embodiment of the present invention the at least one compound comprises isotretinoin (13-cis-retinoic acid).

In a very preferred embodiment of the present invention the at least one compound is selected from the group comprising isotretinoin (13-cis-retinoic acid), fenretinide and etretinate.

In specific embodiments of the present invention, said at least one compound is not all-trans-retinoic acid and/or said at least one compound is not 9-cis-retinoic acid, i.e. the at least one compound is any of the above-mentioned compounds, except all-trans-retinoic acid and/or 9-cis-retinoic acid.

A preferred embodiment of the present invention thus comprises use of at least one compound in the manufacture of a medicament for prevention or treatment of a non-degenerative retinal disorder, or associated symptoms and complications thereof in a mammal, including a human being, with the proviso that said at least one compound does not comprise all-trans-retinoic acid and/or 9-cis-retinoic acid.

Another embodiment comprises a method for prevention or treatment of a non-degenerative retinal disorder, or associated symptoms and complications thereof, in a mammal, including a human being, comprising administering to said mammal, including a human being, a pharmaceutically efficient amount of at least one compound, with the proviso that said at least one compound does not comprise all-trans-retinoic acid and/or 9-cis-retinoic acid.

Non-Degenerative Retinal Disorders

In a much-preferred embodiment of the present invention, the disease to be treated or prevented is a non-degenerative retinal disorder. Non-degenerative diseases of the eye that can be treated or prevented with said therapeutic agent include, but is not limited to, diabetic retinopathy and other small vessel disorders associated with diabetes, such as the advanced stages of diabetic retinopathy, namely diabetic macular edema and diabetic proliferative retinopathy. Other non-degenerative diseases treatable or preventable with compounds capable of inhibiting the visual cycle and/or dark adaptation include retinopathy of prematurity, branch retinal vein occlusion, central retinal vein occlusion, branch retinal artery occlusion, central retinal artery occlusion, subretinal neovascularization, sickle-cell retinopathy, macroglobulinemic and other hyperviscous retinopathies, radiation retinopathy, glaucoma, optic neuritis, and other optic neuropathies, and rubeosis of the iris and the more advanced stages of the same condition that is neovascular glaucoma.

In a preferred embodiment of the present invention, said mammal or human being treated with said medicament has been diagnosed with diabetes. In a very preferred embodiment of the present invention, the non-degenerative retinal disorder prevented or treated with said medicament is diabetic retinopathy (preproliferative or proliferative diabetic retinopathy) or a disorder associated with diabetic retinopathy, such as macular edema, angioproliferation, or neovascularization.

In one aspect of the invention, a method for treating and/or preventing diabetic retinopathy, or associated symptoms or complications thereof, in a mammal, including a human being, is provided.

Advantageously, in one embodiment the method includes the identification of a subject afflicted with diabetes, and the administration of a pharmaceutically acceptable solution containing a pharmaceutically efficient amount of at least one compound capable of inhibiting the visual cycle and/or dark adaptation.

Pharmaceutical Compositions

In a further main aspect, the invention relates to a pharmaceutical composition suitable for intravitreal implantation comprising a pharmaceutically effective amount of at least one compound capable of inhibiting the visual cycle and/or dark adaptation, preferably one of the compounds described specifically herein.

Pharmaceutical compositions or medicaments of the present invention comprising compounds capable of inhibiting the visual cycle and/or dark adaptation, include all compositions wherein at least one pharmaceutical compound or composition is contained in an amount effective to achieve its intended purpose.

In addition, pharmaceutical compositions of the present invention may contain suitable pharmaceutically acceptable carriers comprising excipients and auxiliaries which facilitate processing of the active compounds into preparations which can be used pharmaceutically.

Pharmaceutically acceptable carriers may comprise physiologically active compounds that act, for example, to stabilize the composition, and/or to increase or decrease the absorption of the agent. Physiologically acceptable compounds may include, for example, carbohydrates, such as glucose, sucrose, or dextrans, anti-oxidants, such as ascorbic acid or glutathione, chelating agents, low and/or high molecular weight proteins, compositions that reduce the clearance or hydrolysis of the at least one compound, or excipients or other stabilizers and/or buffers. Other physiologically acceptable compounds include wetting agents, emulsifying agents, dispersing agents or preservatives which are particularly useful for preventing the growth or action of microorganisms.

Because most retinoids are lipid soluble the use of solubilizers and/or emulsifiers is often desired to produce aqueous retinoid solutions or emulsions. Such solubilizers and emulsifiers are well known to those of skill in the art.

Administration

The compounds and/or compositions of the present invention are to be administered preferably to mammalian recipients, most preferably to human beings.

The route of administration may be systemic (e.g. oral, parenteral), topical (e.g. eye drops), or local, such as by intravitreal, subretinal, or subtenonal injection or infusion. In one preferred embodiment of the invention the route of administration is local by intraocular injection or infusion. In another preferred embodiment the at least one compound is in a device formulation held confined by mechanical or physicochemical effects. In yet another preferred embodiment the at least one compound is in a slow-release formulation. However, a person skilled in the art will appreciate that other effective methods of administration are contemplated by the invention.

One very preferred embodiment of the present invention comprises administering by intraocular injection at least one active agent in a slow-release device formulation to a subject afflicted with diabetes.

Dosages and Schedules

A pharmaceutically efficient amount of at least one compound capable of inhibiting the visual cycle and/or dark adaptation is employed in treatment or prevention of a subject. The dosages and repetition interval (the timing of retreatment) of the drug, in the development of the drug formulation as well as in clinical practice, can be adjusted on the basis of titration tests known to persons skilled in the art.

In one embodiment of the present invention the pharmaceutically efficient amount of the at least one active agent is determined as an amount efficient to reduce dark adaptation as measured by conventional methods known to the skilled person. Examples of such tests include, but are not limited to, electrophysiological measurements (electroretinography, primarily scotopic electroretinography), conventional dark adaptometry according to the method of Goldmann-Weekers or a comparable method, and simple standardized stochastic threshold tests that can be applied outside ophthalmological clinics, e.g. in family practice or in the patient's own home, where the patient could, for example, rest in a completely darkened room for a period of standard length, typically one half hour, and then determine by herself or himself whether a standard luminosity object can be seen or not seen, or a combination of these procedures. In the latter case, the luminous standard object, i.e. a very weak lamp, should be invisible when therapeutic action has been achieved, and should become visible when the therapeutic action has tapered and approaches the level where renewed administration of the therapeutic agent is needed. Consequently, the therapeutic level of night vision suppression is defined and monitored by the patient's response, one eye at a time, to a simple non-invasive test.

Additional means of dosage and readministration interval titration include flicker photometry and fundus reflectometry before and after dark adaptation or during the dark adapted stages only. It is understood that the most complete level of dark adaptation which can be achieved by an individual during treatment may be characterized by absence of normal dark adaptation.

Further methods of achieving optimal dosage and readministration interval include determination of changes in retinal blood flow using fundus photographic, angiographic, laser-doppler based or laser-speckle based methods. Fundus photographic methods of estimating retinal blood flow include measurement of changes in retinal vessel diameter and circulation time. Methods of monitoring the effect of treatment include measurement of changes in retinal thickness using optical coherence tomography and visual grading of the level of diabetic retinopathy or other types of retinal disease.

Specific means of estimating the dose required may include determination of a given patient's stores of vitamin A, vitamin A precursors, and vitamin A metabolites such that patients with low body stores of such vitamin receive less of the therapeutic agent, etc.

It is understood that the dosage of a pharmaceutical compound or composition of the present invention administered in vivo will be dependent upon the age, sex, health, and weight of the recipient, kind of concurrent treatment, if any, frequency of treatment, and the nature of the pharmaceutical effect desired. The ranges of effective doses provided herein are not intended to be limiting and represent preferred dose ranges. However, the most preferred dosage will be tailored to the individual subject, as is understood and determinable by one skilled in the relevant art.

An example of the dosage range of compound required to achieve a clinical effect using systemic administration would be 1 mg of isotretinoin per kg body weight per day to 80 mg of isotretinoin per kg body weight per day. When administered inside the eye or adjacent to the eye, the total dosage per day per eye should be within the range from 1 µg to 1000 µg, the higher dosages being of particular relevance when means of inducing protracted release of active compound are applied.

Supplementary systemic administration of vitamin A and/or local administration of vitamin A or its related compounds to the surface of the eye (topical instillation of eye drops into the conjunctival sac) may be of value in reducing side-effects of the therapeutic agent owing to its escape from the inside of the eye.

Formulations

The formulation may be a water solution. Alternatively, the formulation may comprise a slow-release formulation or device wherein the active agent is held confined by mechanical or physico-chemical effects, including polymer binding, copolymerization, embedding of the active compound in polymers, gels, solids and other substances, adsorption and other types of non-covalent binding. Also included is covalent binding that confers inactivity or sequestration in the bound form together with mechanisms of gradual release that increase or otherwise alter the pharmacokinetic profile of the active agent. Examples of such sustained-release systems include semi-permeable polymer matrices in the form of shaped articles (e.g., films or microcapsules). Furthermore, various slow-release polymeric devices have been developed and tested in vivo in recent years for the controlled delivery of drugs. A variety of biocompatible polymers (including hydrogels), including both biodegradable and non-degradable polymers, can be used to form an implant for the sustained release of an invention composition at a particular target site. The generation of such implants is generally known in the art. The present invention is however not confined to the above-mentioned formulations and the skilled person will appreciate that other formulations for effective administration are contemplated by the invention.

The pharmaceutically active compounds may be crystallized as a salt or salts using any counterion that confers to the salt a solubility that is sufficiently rapid or sufficiently slow to provide a desired pharmacokinetic and/or pharmacodynamic profile, as can be determined using conventional kinetics of dissolution assays, microscopic visualization of crystals in the vitreous of the eye, preferably using cross-polarization examination, and dark adaptometric or spectrophotometric examination of the eye.

The pharmaceutically active compounds may be attached covalently to a delivery-enhancing transporter by chemical or recombinant methods and referred to as pro-drugs in that the release (e.g., by degradation or specific cleavage) of the delivery-enhancing transporters from the drugs results in the conversion of the drug from an inactive to an active form. For example, the pro-drug may be produced by esterification, e.g. as a di-X-acetonide, where X is a retinoid. Furthermore, the drug or pro-drug, or a combination of the two, may be crystallized and administered in pure microcrystalline form, in a mixture of crystals with a combination of sizes and coatings that convey a desired and predetermined pharmacokinetic profile and/or susceptibility to disruption by photocoagulation or photodisruptive lasers that may confer lack of drug release or drug release at only low rates before disruption, whereas after non-invasive disruption an increased rate of release from the inactive solid form into water solution inside the eye can be achieved.

REFERENCES

1. Crouch, R. K., Chader, G. J., Wiggert, B., and Pepperberg, D. R. (1996). Photochem. Photobiol. 64, 613-621.
2. Hecht, S., and Mandelbaum, J. (1938). Science 88, 219-221.
3. Dowling, J. E., and Wald, G. (1958). Proc. Natl. Acad. Sci. USA 44, 648-661.
4. Weleber, R. G., Denman, S. T., Hanifin, J. M. and Cunningham, W. J. (1986). Arch. Ophthalmol. 104, 831-837.
5. Maclean, H., Wright, M., Choi, D., Tidman, M. J. (1995). Clin. Exp. Dermatol. 20, 86
6. Fraunfelder, F. T., Fraunfelder, F. W., and Edwards, R. (2001). Am. J. Ophthalmol. 132, 299-305.
7. Law, W. C., and Rando, R. R. (1989). Biochem. Biophys. Res. Comm. 161, 825-829.
8. Welsh, B. M., Smith, A. L., Elder, J. A., and Varigos, G. A. (1999). Australas J Dermatol. 40, 208-10.
9. Moss, G. P. (1983). Arch. Biochem. Biophys. 224, 728-731 and http://www.chem.gmul.ac.uk/iupac/misc/ret.html
10. Sani, B. P., and Hill, D. L. (1990). Meth. In Enzymology. 189, 43-59.
11. Klaus, M. (1990). Meth. In Enzymology. 189, 3-14.
12. Dawson, M. I., and Hobbs, P. D. (1990). Meth. In Enzymology. 189, 15-43.
13. Gollapalli, D. R. and Rando, R. R. (2003). Biochim. Biophys. Acta. 1651, 93-101.
14. Arden, G. B. (2001). Br. J. Ophthalmol. 85, 366-370.
15. Acland, G. M., Aguirre, G. D., Ray, J., Zhang, Q., Aleman, T. S., Cideciyan, A. V., Pearce-Kelling, S. E., Anand, V., Zeng, Y., Maguire, A. M., Jacobson, S. G., Hauswirth, W. W., and Bennett, J. (2001). Nature Genetics. 28, 92-95.
16. Redmond, T. M., Yu. S., Lee, E., Bok, D., Hamasaki, D., Chen, N., Goletz, P., Ma, J. X., Crouch, R. K., and Pfeifer, K. (1998). Nature Genetics. 20, 344-351.
17. Bernstein, P. S., and Rando, R. R. (1985). Vision Res. 25, 741-748.
18. Bernstein, P. S., Fulton, B. S., and Rando, R. R. (1986). Biochemistry. 25, 3370-3377.

EXAMPLES

Example 1

Resistance to Retinal Ischemia 1 h after Intraperitoneal Isotretinoin

Purpose: To evaluate the efficacy of isotretinoin in the prevention of retinal functional loss following 1 h of ocular ischemia induced by elevation of the intraocular pressure beginning 1 h after the intraperitoneal administration of isotretinoin.

Material and methods: Of 12 Sprague-Dawley rats, 7 received intraperitoneal saline injection and 5 received intraperitoneal isotretinoin 5 mg/kg in dimethyl sulfoxide (DMSO) 1 h before intraocular pressure elevation during full anaesthesia using cannulation of the anterior chamber in one eye and infusion of balanced saline solution at a pressure of 110 mmHg. The fellow eye was not subjected to ischemia. The animals were kept in ambient room light before and during ischemia. Retinal function was assessed 1 week later by scotopic and mesopic full-field electroretinography (ERG). The study adhered to the ARVO resolution on animal welfare.

Results: All 12 eyes not subjected to ischemia had normal scotopic ERG amplitudes (60-120 µV) 1 week after ischemia. All 7 eyes subjected to ischemia without prior administration of isotretinoin had flat ERGs (no signal above baseline fluctuation±3.5 µV). Of 5 eyes subjected to ischemia after the animals had received isotretinoin, intact scotopic ERG was found in 3 animals and flat ERG in 2 animals.

Conclusion: In this study, systemic isotretinoin treatment was associated with preservation of normal retinal function in the majority of eyes subjected to transient ischemia sufficient to eliminate retinal function in all untreated eyes. Failure to preserve retinal function in two animals was likely attributable to delayed absorption of intraperitoneal isotretinoin.

Example 2

Resistance to Retinal Ischemia 24 h after Intraperitoneal Isotretinoin

Purpose: To evaluate the efficacy of isotretinoin in the prevention of retinal functional loss following 1 h ischemia induced by elevation of the intraocular pressure beginning 18 h after the intraperitoneal administration of isotretinoin.

Material and methods: Intraperitoneal isotretinoin 5 mg/kg in dimethyl sulfoxide (DMSO) was given to 6 Sprague-Dawley rats 18 h before intraocular pressure elevation during general anesthesia using cannulation of the anterior chamber in one eye and infusion of balanced saline solution at a pressure of 110 mmHg. The fellow eye was not subjected to ischemia. The animals were kept in ambient room light before and during ischemia. Retinal function was assessed 1 week later by scotopic and mesopic full-field electroretinography (ERG). The study adhered to the ARVO resolution on animal welfare.

Results: All 6 eyes subjected to ischemia in isotretinoin-treated animals had normal scotopic ERG amplitudes (60-120 µV) 1 week after ischemia.

Conclusion: In this study, systemic isotretinoin treatment was associated with preservation of normal retinal function in all eyes subjected to transient ischemia sufficient to eliminate retinal function in untreated eyes (see experiment 1; p=0.02). The effect of intraperitoneal isotretinoin was better 18 h after injection than 1 h after injection, suggesting absorption of therapeutic levels of isotretinoin can be achieved in all animals within 18 h.

Example 3

Reduction of Retinal Flow after Intraocular Administration of Isotretinoin

Purpose: To assess the effect of intravitreal isotretinoin on retinal vessel diameters in rats, the vein diameter acting as a marker of retinal flow and metabolism.

Methods: In 6 animals, one eye received a single intravitreal injection of isotretinoin 2.5 μg in 10 μl dimethyl sulfoxide (DMSO). The fellow eye received a placebo injection of 10 μl DMSO. Retinal vessel diameter was recorded 6 h later in both eyes after the rats had dark adapted using digital fundus photography in red illumination and assessed using computerized image analysis. All procedures were performed in general anesthesia and the study adhered to the ARVO resolution on animal welfare.

Results: Both eyes were intact in 4 animals, 1 eye in one animal suffering from retinal detachment and 1 eye in 1 animal from vitreous hemorrhage. In 4 isotretinoin-treated eyes a change in retinal vein diameter of −9% (SD 4.2%) was observed, whereas in placebo-treated eyes the change was −0.75% (SD 4.8%)(p=0.04).

Conclusion: Intravitreal isotretinoin treatment was associated with a reduction in retinal vein diameter, supporting that isotretinoin treatment induces a reduction of retinal blood flow secondary to a decrease in retinal metabolism. Because retinal hyperperfusion is likely to contribute to the pathogenesis of diabetic retinopathy, isotretinoin treatment is of theoretical therapeutic benefit in this condition.

Example 4

Experimental Retinal Vein Occlusion

Purpose: To assess the effect of isotretinoin on the integrity of the blood-retina barrier in experimental retinal vein occlusion.

Material and methods: Occlusion of all retinal veins near the rim of the optic nerve head was induced by laser photocoagulation in 14 rats. Blood-retina barrier permeability was measured using vitreous fluorometry 2 weeks later. In 7 rats, intraperitoneal isotretinoin 5 mg/mild in dimethyl sulfoxide (DMSO) was administered for five days before the examination of vascular leakage 14 days after photocoagulation. The study adhered to the ARVO resolution on animal welfare.

Results: Compared to untreated animals, retinal vascular leakage was lower in eyes of animals treated with isotretinoin than in eyes of animals not treated with isotretinoin (p<0.012).

Conclusion: Systemic isotretinoin treatment was associated with better blood-retina barrier function in experimental retinal vein occlusion.

REFERENCES

Adamis A P et al.: Inhibition of vascular endothelial growth factor prevents retinal ischemia-associated iris neovascularization in a nonhuman primate. Arch Ophthalmol. January 1996; 114(1):66-71.
Hikichi T et al.: Inhibitory effects of bucillamine on increased blood-retinal barrier permeability in streptozotocin-induced diabetic rats. Curr Eye Res. (2002) 25(1):1-7.
Kohner E M: The effect of diabetic control on diabetic retinopathy. Eye 1993; 7:309-311.
Larsen M et al.: Protective Effect of Captopril on the Blood-Retina Barrier in Normotensive Insulin-Dependent Diabetic Patients with Nephropathy and Background Retinopathy. Graefe's Arch Clin Exp Ophthalmol 228:505-509, 1990.
Mukaida Y et al.: Correlation of retinal function with retinal histopathology following ischemia-reperfusion in rat eyes. Curr Eye Res. June 2004; 28(6):381-9.
Ozbay D: Protective effect of ischemic preconditioning on retinal ischemia-reperfusion injury in rats. Can J Ophthalmol. December 2004; 39(7):727-32.
Pedersen L et al: Quantitative measurement of changes in retinal vessel diameter in ocular fundus images. Pattern Recognition Letters 21:1215-1223, 2001.

The invention claimed is:

1. A method of reducing risk of, or treating, non-proliferative diabetic retinopathy and/or macular edema, in a mammal by administrating an effective amount of a medicament comprising at least one compound capable of inhibiting the visual cycle, to said mammal, wherein said compound is fenretinide defined by formula V:

(formula V)

wherein R1, R4, R9, R10 and R12 is CH3, and R3, R5, R6, R7, and R8 is H, and
wherein R11 is
—CONHR', wherein R' is 4-hydroxy-phenyl, and
wherein the configuration of the four isoprenoid units is all trans (E).

2. The method of claim 1, wherein said mammal is a human being.

3. The method of claim 1, wherein said mammal has been diagnosed with diabetes.

4. The method of claim 1, wherein the medicament is in a form for being administered locally.

5. The method of claim 4, wherein the medicament is in a form for being administered intravitreally.

6. The method of claim 1, wherein the medicament is in device formulation held confined by mechanical or physico-chemical effects.

7. The method of claim 1, wherein the medicament is in a slow-release formulation.

8. The method of claim 1 which is a method of treating non-proliferative diabetic retinopathy and/or macular edema.

9. The method of claim 1 which is a method of treating non-proliferative diabetic retinopathy.

* * * * *